United States Patent
Delegge et al.

(10) Patent No.: US 8,900,195 B2
(45) Date of Patent: Dec. 2, 2014

(54) EXTERNAL BOLSTER

(75) Inventors: Mark Delegge, Mount Pleasant, SC (US); Becky Delegge, Mount Pleasant, SC (US); Hilbert Brown, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/216,422

(22) Filed: Aug. 24, 2011

(65) Prior Publication Data

US 2012/0053525 A1   Mar. 1, 2012

Related U.S. Application Data

(60) Provisional application No. 61/376,507, filed on Aug. 24, 2010.

(51) Int. Cl.
*A61M 5/32* (2006.01)
*A61M 39/02* (2006.01)
*A61J 15/00* (2006.01)
*A61M 25/02* (2006.01)

(52) U.S. Cl.
CPC ........ *A61M 39/0247* (2013.01); *A61J 15/0061* (2013.01); *A61J 15/0015* (2013.01); *A61M 2025/0233* (2013.01); *A61M 2039/0255* (2013.01); *A61M 2039/0261* (2013.01); *A61M 2039/0282* (2013.01); *A61M 2039/0294* (2013.01)
USPC .......................................... 604/174; 604/175

(58) Field of Classification Search
USPC .......................... 604/174, 175, 177, 178, 180
See application file for complete search history.

(56) References Cited

U.S. PATENT DOCUMENTS

| 3,444,861 | A |   | 5/1969  | Schulte           |         |
|-----------|---|---|---------|-------------------|---------|
| 3,976,080 | A |   | 8/1976  | Bornhorst et al.  |         |
| 4,315,513 | A | * | 2/1982  | Nawash et al.     | 604/537 |
| 4,435,174 | A |   | 3/1984  | Redmond et al.    |         |
| 4,645,492 | A |   | 2/1987  | Weeks             |         |
| 5,484,420 | A |   | 1/1996  | Russo             |         |
| 5,556,385 | A |   | 9/1996  | Andersen          |         |
| 5,690,616 | A |   | 11/1997 | Mogg              |         |
| 5,720,734 | A |   | 2/1998  | Copenhaver et al. |         |

(Continued)

FOREIGN PATENT DOCUMENTS

CA   2 242 557       10/2006
GB   2 147 811  A    5/1985

(Continued)

OTHER PUBLICATIONS

Notification of Transmittal of the International Search Report and the Written Opinion of the International Searching Authority, or the Declaration, dated Dec. 5, 2011, for PCT/US2011/048903, 5p.

(Continued)

*Primary Examiner* — Kami A Bosworth
(74) *Attorney, Agent, or Firm* — Brinks Gilson & Lione

(57) ABSTRACT

An external bolster having a main body, a curved portion and a hinge. The bolster also includes a base fixably attached to the main body, the base including a spoke configured to allow air through the base and a cap removably attached to the main body at the hinge, wherein the cap is configured to position a tube along the curved portion of the main body when the cap is in a closed position.

15 Claims, 3 Drawing Sheets

(56) References Cited

U.S. PATENT DOCUMENTS

| | | |
|---|---|---|
| 6,165,168 A | 12/2000 | Russo |
| 6,458,106 B1 | 10/2002 | Meier et al. |
| 6,482,183 B1 * | 11/2002 | Pausch et al. ............ 604/174 |
| 7,549,200 B2 | 6/2009 | McMichael et al. |
| 7,641,648 B2 | 1/2010 | Bouphavichith et al. |
| 8,303,549 B2 * | 11/2012 | Mejlhede et al. ............ 604/244 |
| 2003/0032932 A1 | 2/2003 | Stout |
| 2003/0120260 A1 | 6/2003 | Chu et al. |
| 2003/0212385 A1 | 11/2003 | Brenner et al. |
| 2003/0225393 A1 | 12/2003 | McMichael et al. |
| 2005/0010195 A1 | 1/2005 | Bouphavichith et al. |
| 2005/0096750 A1 | 5/2005 | Kagan et al. |
| 2006/0052752 A1 | 3/2006 | McMichael |
| 2006/0078575 A1 | 4/2006 | Goldberg |
| 2006/0100604 A1 | 5/2006 | Brenner et al. |
| 2006/0135914 A1 | 6/2006 | Chu et al. |
| 2007/0156117 A1 | 7/2007 | Adams et al. |
| 2007/0276356 A1 | 11/2007 | Downing et al. |

FOREIGN PATENT DOCUMENTS

| | | |
|---|---|---|
| WO | WO 0032260 A1 | 6/2000 |
| WO | WO 0160313 A1 | 8/2001 |
| WO | WO 2007/033340 A2 | 3/2007 |

OTHER PUBLICATIONS

Notification of Transmittal of the International Search Report and the Written Opinion of the International Searching Authority, or the Declaration issued Mar. 10, 2011 in Appln. No. PCT/US2010/061732 (10 pages).

* cited by examiner

EXTERNAL BOLSTER

RELATED APPLICATION

The present patent document claims priority to, the benefit of the filing date, and all other benefits under 35 U.S.C. §119(e) and all other applicable statutes of U.S. Provisional Patent Application Ser. No. 61/376,507 filed Aug. 24, 2010, which is hereby incorporated by reference in its entirety.

BACKGROUND

The present system relates to medical devices, and more particularly, to low-profile external fittings for systems that deliver materials to the interior of a body cavity.

Patients for which normal ingestion of food becomes difficult or impossible may require placement of a feeding tube to assist in providing their nutritional needs. For some individuals, such as comatose patients, stroke victims, or those with a compromised gastrointestinal tract and the like, this may require placement of a tube that is introduced percutaneously into the stomach for delivery of nutritional products directly into the stomach or jejunum. The procedure, known as a Percutaneous Endoscopic Gastrostomy (PEG) can be performed using several different techniques. Some techniques include the introduction of an endoscope into the stomach. The desired site where the stoma is to be created is indicated from above by depressing the abdomen and viewing the depressed site with the endoscope. Transillumination may also be utilized to locate the desired site through the abdominal wall. A sheathed needle or trocar punctures the abdominal wall and enters the stomach, creating a stoma. The needle is removed and a looped insertion wire/suture is introduced through the sheath where it is grasped by a snare or forceps deployed from the working channel of the endoscope. Once it is captured, the insertion wire/suture is pulled into the working channel of the endoscope. The endoscope is then withdrawn from the patient via the oral cavity, pulling the insertion wire/suture with it.

In the standard Ponsky method (or "pull" method), the distal loop of a percutaneous gastrostomy feeding tube is coupled to the insertion wire/suture exiting the patient's mouth. With the insertion wire/suture now tethered to the gastrostomy feeding tube, the endoscopist retracts the portion of the insertion wire/suture exiting the stoma, thereby pulling the gastrostomy feeding tube into the patient's mouth and towards the stomach. With continued retraction of the insertion wire/suture, the distal end of the gastrostomy feeding tube is pulled out through the stoma. The gastrostomy feeding tube typically includes a tapered dilator portion to aid its passage through the stoma. Once the feeding tube has been properly positioned with the proximal end cap or bolster of the feeding tube against the internal wall of the stomach, it is secured by an external bolster positioned against the outside of the abdomen wall.

In a variation of the PEG procedure known as the "push" method, the gastrostomy feeding tube is advanced or pushed down the esophagus by the physician and into position in the stomach using a wire guide that has been placed in the same manner as the insertion wire in the "pull" method. More specifically, the feeding tube is loaded on the portion of the wire guide exiting the patient's mouth by passing the end of the wire guide through a lumen extending through the length of the feeding tube. While holding the wire guide stationary, the physician pushes the feeding tube along the wire guide through the patient's mouth, into the stomach, and then out through the stoma. The feeding tube is then secured in the same manner as the "pull" method.

Yet another method is simply to insert the feeding tube through the patient's abdominal wall using the Seldinger technique and bypass insertion through the mouth. However, this method typically requires the deployment of an internal retention device including, and/or in addition to attaching a bolster to the interior portion of the feeding tube, which may need to be delivered and attached endoscopically.

As stated above, typically, a retention bolster is positioned against the inside and/or outside of the abdomen wall, or whichever body cavity or area the gastric port is being used in relation to. The bolster is present to keep in place and support the gastric port system and prevent sudden or unexpected removal of the tube from the stoma site. Bolsters for supporting tubes, such as feeding tubes, inside or outside the body have generally focused on maintaining the secure anchoring of the device to the patient. To provide support, bolsters have employed flanges, cross-bars, discs, or balloons for contacting the surface of the tissue. In the past, however, bolsters have tended to increase the localized pressure at the exit site, especially when the port or tube, either accidentally or intentionally, is moved thereabout.

For both ambulatory and bed-ridden patients, an external length of feeding tube and/or feeding apparatus may be connected to and removed from an external fitting of the tube, with or without an external bolster. Different diameters and lengths of tube may be needed. Depending on application, the system may need to be present with the patient for an extended period of time. Many current bolsters have a large and/or awkward profile such that extended use makes them uncomfortable for the patient where normal bodily movement is necessary.

A need therefore exists for a bolster that has a lower profile that is configured for use adjacent to a body surface that can decrease the localized pressure at the exit site, especially when the tube and/or bolster, either accidentally or intentionally, is moved thereabout.

BRIEF SUMMARY

The foregoing problems are solved and technical advance is achieved with an illustrative external bolster.

These and other advantages, as well as the external bolster and gastric port system, will become apparent in the details of construction and operation as more fully described below. Moreover, it should be appreciated that several aspects of the invention can be used with other types of gastric port systems or medical devices.

DETAILED DESCRIPTION OF THE DRAWINGS AND THE PRESENTLY PREFERRED EMBODIMENTS

For the purposes of promoting an understanding of the principles of the external bolster, reference will now be made to the embodiments illustrated herein. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the discovery relates.

Figure 1:
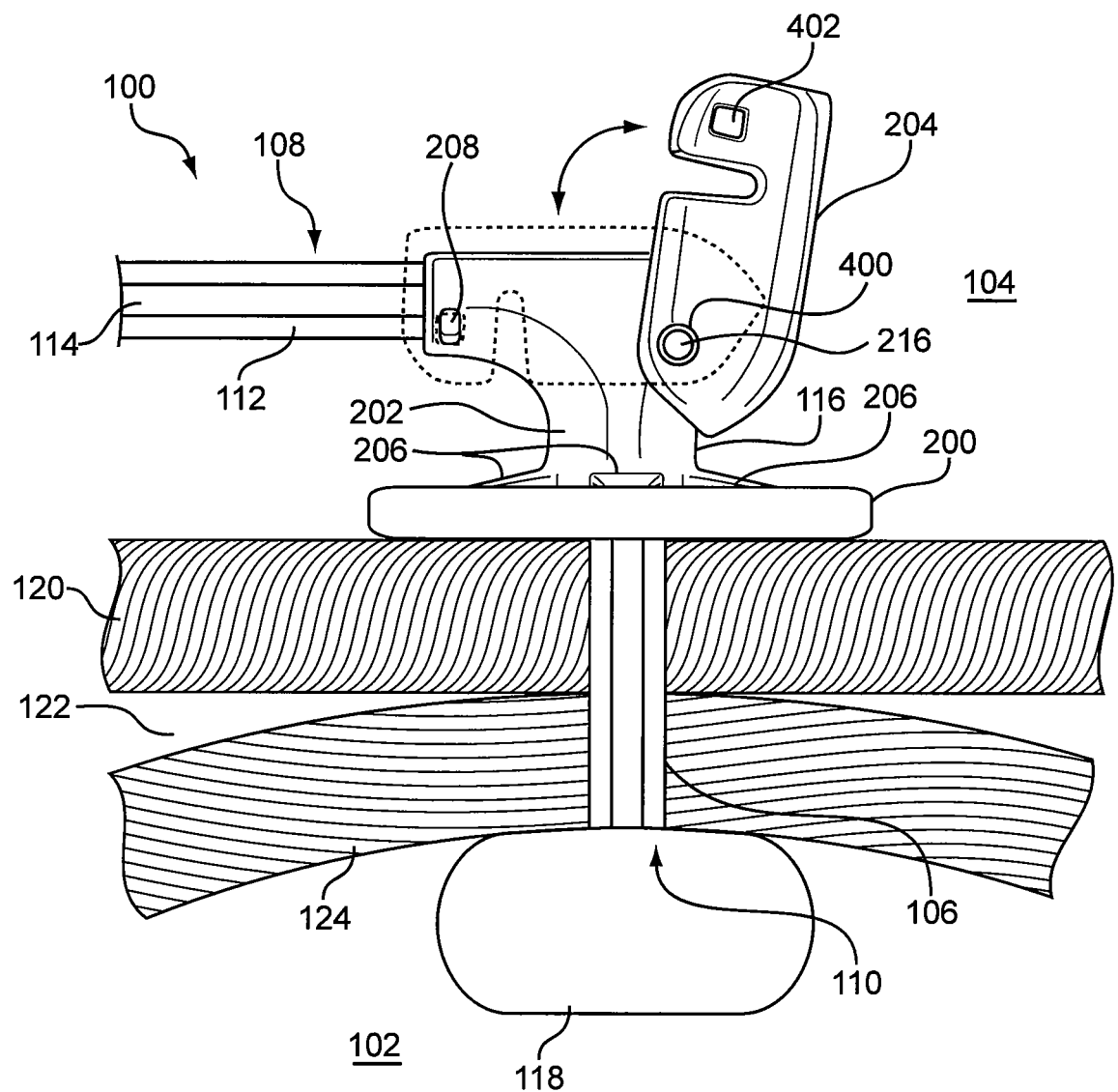
FIG. 1 is an illustration of a gastric port system.

Referring now to FIG. 1, a gastric port system 100 is illustrated traversing a stoma between a first body cavity 102 and an area 104 adjacent to the first body cavity 102. More specifically, and as illustrated in FIG. 1, the first body cavity 102 may be the abdominal cavity of the patient, and area 104 illustrated is an area external to the patient. However, the first body cavity 102 may be any body cavity that would benefit from the advantages disclosed herein.

Gastric port system 100 includes a tube or port 106 that has a proximal portion 108 and a distal portion 110. The proximal portion 108 may be defined as the portion of the tube 106 that extends into area 104 and the distal portion 110 may be defined as the portion of the tube 106 that extends into the first body cavity 102 such that it about flush with the internal bolster 118. The tube 106 also includes a passageway 112 that allows for the passage of materials through the tube 106. More specifically, the passageway 112 allows for the passage of nutritional products or medications directly into the body or body cavity 102 of a patient. Alternatively, a catheter 114 may be introduced to extend through the passageway 112 and may act as the delivery mechanism for materials directly into the body or body cavity 102 of a patient. The tube 106 may be made of any material suitable for the placement of the tube 106 into a body or body cavity 102 of a patient. Likewise, the catheter 114 may be made of any material suitable for delivery of, for example, nutritional products, or medications into the body or body cavity 102.

An external bolster 116 and an internal bolster 118 are illustrated in FIG. 1. The external bolster 116 may be slidable relative to the tube 106. The internal bolster 118 may be fixably attached to the distal portion 110 of the tube 106. The external bolster 116 may be slidably disposed on the proximal portion 108 of the tube 106. The external bolster 116 and the internal bolster 118 may be different sizes and shapes. For example, the external bolster 116 may be molded or machined from a solid piece of material, such as medical grade silicone. Alternatively, the external bolster 116 may be formed such that the components thereof are formed as unitary structures and then assembled. Similarly, the internal bolster 118 may be molded or machined from a solid piece of material, such as medical grade silicone and the like and may be ring shaped, bowl shaped, T-shaped, Malecot shaped, mushroom shaped, dome shaped, conical shaped, or any other shape that can provide retention for the tube or port 106.

FIG. 1 illustrates the external bolster 116 engaging the first side of abdomen wall 120. Adjacent to the abdomen wall 120 and the gastric wall 124 is the peritoneum cavity 122. However, use of the device is not limited to the abdominal area. Other bodily areas are contemplated such that a cavity 122 or one or more walls 120, 124 may be the space or material separating or adjacent to a body cavity 102 and area 104. The internal bolster 118 is also illustrated engaging the second side of the gastric wall 124.

Referring now to FIGS. 1-6, the external bolster 116 of FIG. 1 is illustrated. The external bolster 116 includes a base 200, a main body 202, to which the base 200 is attached, and a cap 204. Preferably, the cap 204 and the main body 202 are made from polyacetal, but any material suitable for the application described herein may be used. Preferably, the base 200 is made from thermoplastic elastomer, but any material suitable for the application described herein may be used. Preferably, as illustrated for example in FIGS. 1, 2, and 5, the main body 202 is elbow-shaped, illustrated by a curved portion 212 in FIGS. 2 and 5, allowing the tube to exit the external bolster 116 at an opening 210. The curved portion 212 may form an angle of approximately 90 degrees, but the angle may vary and still take advantage of the external bolster 116. Preferably, the external bolster 116 is low profile relative to the abdominal wall 120. A low-profile design of the external bolster 116 allows for the external bolster 116 to minimize being caught on clothing and/or noticeable by others under the patient's clothing.

The base 200 preferably has four spokes 206, but any number of spokes would be suitable to the external bolster system. The spokes 206 serve to allow air flow and/or air to the abdominal wall 120 when the external bolster 116 is in use, and may prevent skin irritation or discomfort. An optional piece of gauze or other material may be disposed between the main body 202 and the abdomen wall 120 to provide cushioning or for any other reason.

Figure 2:
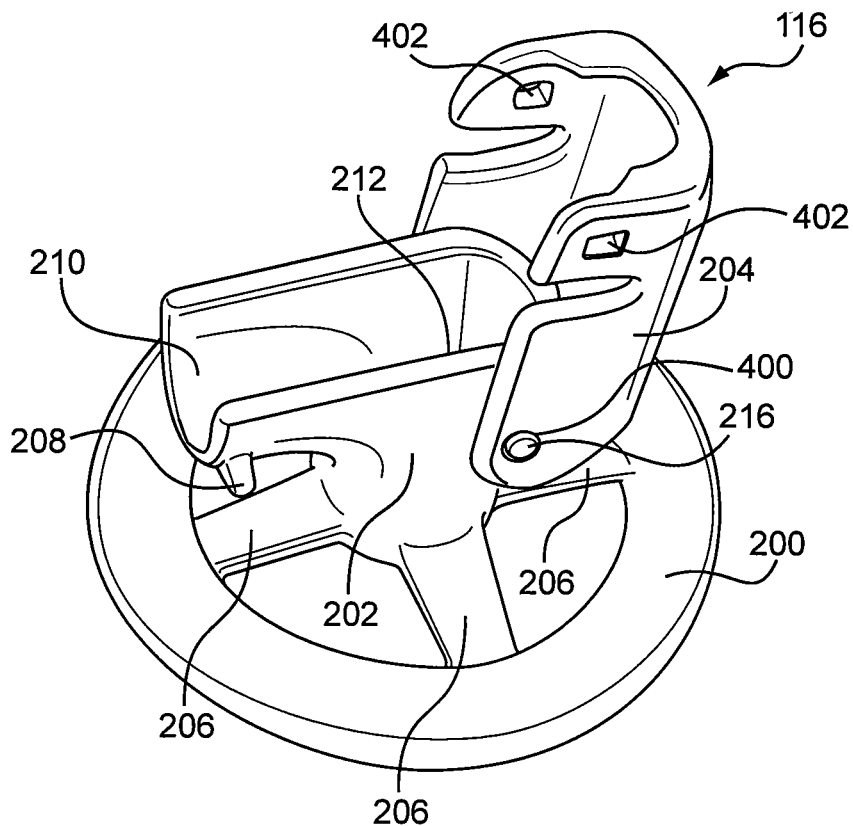
FIG. 2 is a perspective view of the external bolster illustrated in FIG. 1 with the cap in an open position.
Figure 3:
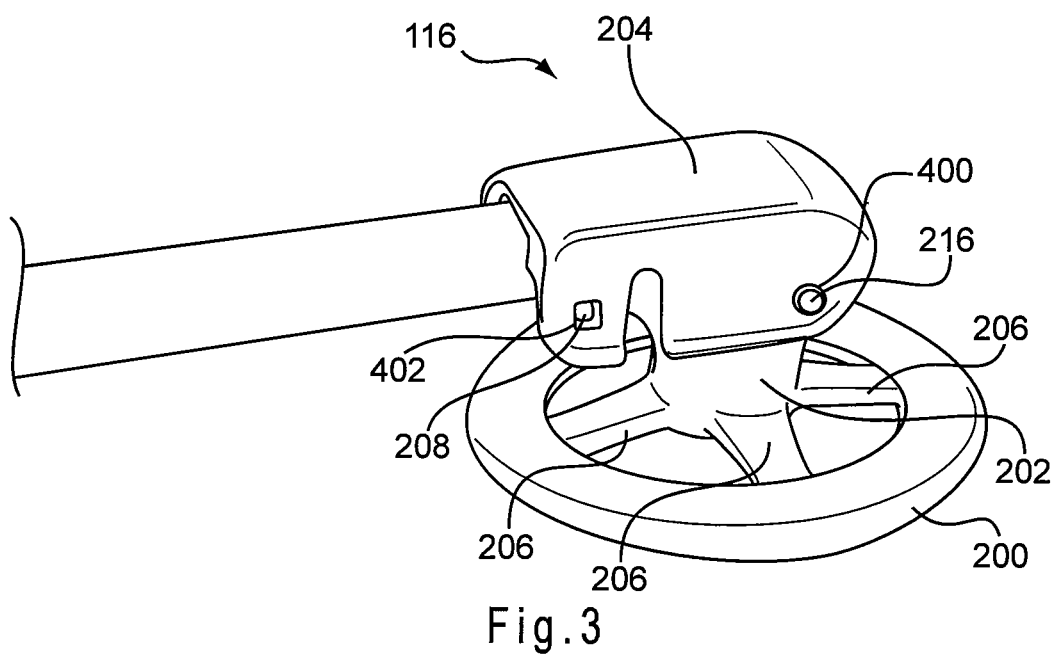
FIG. 3 is a perspective view of the external bolster illustrated in FIG. 1 with the cap in a closed position.
Figure 4:
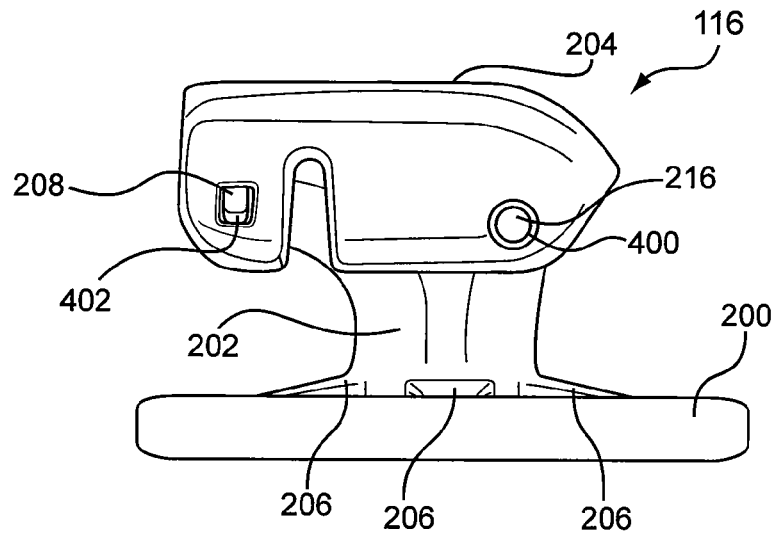
FIG. 4 is a side view of the external bolster with the cap in a closed position.

The main body 202 is curved inside, illustrated by the curved portion 212, which aids in promoting a bend in the tube 106 or otherwise positioning the tube 106 when the tube is inserted into the external bolster 116. The main body 202 and the base 200 preferably are large enough to receive the tube 106, which may be guided within the main body 202 and through the base 200. The main body 202 may include securing pegs 208 that may secure the cap 204 in place when it is in a closed position, as illustrated in FIG. 3. The cap 204 may be attached to the main body 202 at a hinge 216, and may open and close about the main body 202 of the external bolster 116. FIG. 2 illustrates the cap 204 in an open position, and FIG. 3 illustrates the cap 204 in a closed position. The cap 204, when closed, creates a friction fit along with the curved portion 212 to decrease or prevent movement of the tube 106.

Figure 5:
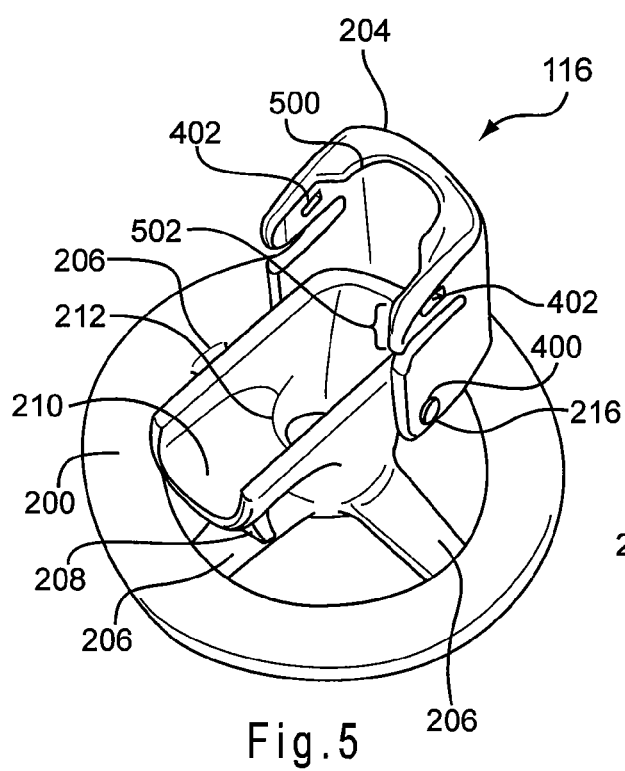
FIG. 5 is a top view of the external bolster with the cap in an open position.
Figure 6:
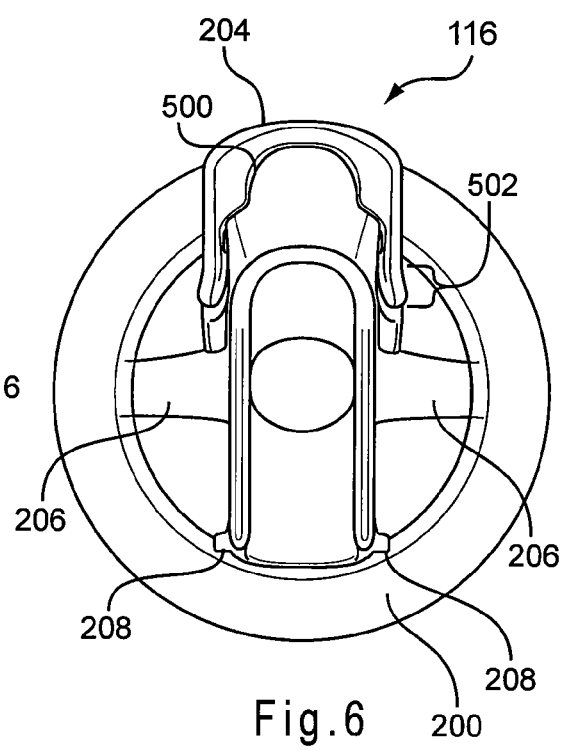
FIG. 6 is a top view of the external bolster with the cap in an open position.

Still referring to FIGS. 1-6, the cap 204 secures the tube 106 when it is inserted in the main body 202 of the external bolster 116. The cap 204 preferably has hinge holes 400 that engage the hinge 216 of the main body 202 such that the cap 204 pivots when the holes 400 are engaged with the hinge 216, allowing the cap 204 to open and close about the main body 202. The cap 204 also preferably has peg holes 402 that engage the securing pegs 208. The peg holes 402 may be located along a flap 502 portion of the cap 204 as illustrated in FIG. 5. The flap 502 portion allows for easier opening and closing of the cap 204 when it is secured to the main body 202 of the external bolster 116. Also illustrated in FIGS. 5 and 6, the cap 204 may have a recessed portion 500 located in the front of the cap 204. The recessed portion 500 may prevent the tube 106 from being pinched or kinked during use, particularly when the cap 204 is in a closed position about the main body 202 of the external bolster 116.

Still referring to FIGS. 1-6, after a stoma is created, the tube 106 may be inserted into the stoma according methods described above. Unlike prior bolsters, however, the external bolster 116 has a low profile. The tube 106 may be positioned by inserting the tube 106 through the main body 202 of the external bolster 116 and down through the base 200 of the external bolster 116. Alternatively, the external bolster 116 may be placed over the tube 106 already in place. When the tube 106 is in a desirable location, the cap 204 may be closed. When the cap 204 is closed, the tube 106 will gently (i.e., preferably without kinking or crimping) curve toward the opening 210 of the main body 202 of the external bolster 116, fitting snugly within the external bolster 116, frictionally securing the tube 106 against longitudinal movement relative to the external bolster 116. To the extent there is any excess portion of the tube 106 protruding out from the external bolster 116, the tube 106 may be cut and that portion may be removed when the cap 204 is closed. As a consequence, the position of the external bolster 116 can be tailored to the patient.

It is therefore intended that the foregoing detailed description be regarded as illustrative rather than limiting, and that it be understood that it is the following claims, including all equivalents, that are intended to define the spirit and scope of this invention.

The invention claimed is:

1. A gastric port system for transport of materials to the interior of a body cavity comprising:
   a tube configured to be disposed between a first body cavity and an area adjacent to the first body cavity and extending through a bodily wall separating the first body cavity from the area adjacent to the first body cavity; the tube further comprising a distal portion, a proximal portion, and a passageway therethrough; and
   an external bolster configured to engage a first side of the bodily wall, the bolster comprising a main body with a curved portion, a base fixably attached to the main body, and a cap pivotally attached to the main body and movable between an open position and a closed position, the main body and the base each being configured for the passage of the tube therethrough, wherein the main body comprises a lower portion and an upper portion, the lower portion being fixedly attached to the base and extending outwardly therefrom, the upper portion being spaced apart from the base and configured to direct the proximal portion of the tube along a pathway that is substantially parallel to and spaced apart from the base, wherein the lower portion comprises a lower surface opposite an upper surface of the base, the lower surface being spaced apart from the upper surface so as to form a gap there between, wherein the cap is pivotally attached to the main body at a location spaced apart from the base, and wherein the closed position of the cap bends the proximal portion of the tube into a right angle and frictionally secures the tube against longitudinal movement relative to the external bolster.

2. The gastric port system of claim 1 further comprising a second bolster configured to engage a second side of the bodily wall and disposed along the distal portion of the tube.

3. The gastric port system of claim 1, wherein the lower portion and the upper portion form an L-shape, the upper portion comprising a hinge, the cap being removably attached to the hinge.

4. The gastric port system of claim 1 further comprising a catheter for the passage of materials, the catheter being removably disposed in the passageway of the tube and extending through at least a portion of the tube.

5. The gastric port system of claim 1, wherein the cap comprises a recessed portion.

6. The gastric port system of claim 1, wherein the cap comprises a plurality of flaps configured to engage the main body and secure the cap in the closed position.

7. The gastric port system of claim 1, wherein the cap comprises a curved recessed portion and a pair of flaps disposed adjacent to the recessed portion, the flaps being configured to engage the main body and secure the cap in the closed position.

8. The gastric port system of claim 1 where the base comprises a plurality of spokes defining open areas there between that are configured to allow air to flow through the base.

9. An external bolster comprising:
   a main body comprising an opening, a curved portion, and a hinge;
   a base extending between an upper surface and a lower surface, the lower surface being configured to engage a first side of a bodily wall, the upper surface fixably attached to the main body, the base comprising a plurality of spokes defining open areas between adjacent pairs of spokes, the open areas extending through the base from the lower surface to the upper surface and configured to allow air flow through the base; and
   a cap removably attached to the main body at the hinge, wherein the cap is configured to position a tube along the curved portion of the main body when the cap is in a closed position,
   wherein the curved portion of the main body forms approximately a right angle having an upper portion that is substantially parallel to and spaced apart from the base so as to form a gap between the upper portion and the base.

10. The external bolster of claim 9 further comprising a securing peg fixably attached to the main body.

11. The external bolster of claim 9, wherein the cap further comprises a recessed portion configured to receive a tube therein, and a hinge hole in communication with the hinge of the main body, the hinge hole and hinge each being spaced away from the base.

12. The external bolster of claim 9 further comprising a tube disposed in the curved portion, wherein the tube comprises a proximal portion that is substantially parallel to and spaced apart from the first side of the bodily wall and the base, and wherein the tube comprises a distal portion that is substantially perpendicular to the first side of the body wall.

13. An external bolster comprising:
   a main body comprising an opening, a curved portion forming an angle of approximately 90 degrees, a hinge, and a securing peg;
   a base fixably attached to the main body, the base comprising a central passage in communication with the opening of the main body, the base further comprising a plurality of open areas configured to allow air to pass through the base, the plurality of open areas extending between a lower surface and an upper surface of the base and being circumferentially disposed about the central passage; and
   a cap removably attached to the main body at the hinge, wherein the cap comprises a recessed portion and a hinge hole in communication with the hinge of the main body, the hinge and hinge hole each being spaced away from the base, the recessed portion of the cap being configured to position a tube along the curved portion of the main body when the cap is in a closed position,
   wherein the curved portion of the main body comprises an end portion that is substantially parallel to and spaced apart from the base such that a gap is formed there between to allow air to pass between the end portion and the base.

14. The external bolster of claim 13 further comprising a tube disposed in the curved portion wherein the tube comprises a proximal portion that is substantially parallel to and spaced apart from a first side of a bodily wall and the base, and wherein the tube comprises a distal portion that is substantially perpendicular to the first side of the body wall.

15. The external bolster of claim 13, wherein the cap comprises a plurality of flaps disposed adjacent to the recessed portion, the flaps being configured to engage the main body and secure the cap in the closed position.

* * * * *